(12) United States Patent
Elmore et al.

(10) Patent No.: US 7,777,076 B2
(45) Date of Patent: Aug. 17, 2010

(54) MACROCYCLIC INHIBITORS OF BCL PROTEINS

(75) Inventors: Steven W. Elmore, Northbrook, IL (US); Christopher L. Lynch, Trevor, WI (US); Xilu Wang, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/914,772

(22) PCT Filed: May 17, 2006

(86) PCT No.: PCT/US2006/019132

§ 371 (c)(1), (2), (4) Date: Feb. 15, 2008

(87) PCT Pub. No.: WO2006/127364

PCT Pub. Date: Nov. 30, 2006

(65) Prior Publication Data

US 2008/0194691 A1    Aug. 14, 2008

Related U.S. Application Data

(60) Provisional application No. 60/684,096, filed on May 24, 2005.

(51) Int. Cl.
  *C07C 321/00* (2006.01)
(52) U.S. Cl. .......................... 564/85; 514/603; 549/346
(58) Field of Classification Search .................. 564/85; 514/603
  See application file for complete search history.

(56) References Cited

U.S. PATENT DOCUMENTS

2002/0086887 A1*  7/2002  Augeri et al. ............... 514/354

OTHER PUBLICATIONS

Jordan, V. C. Nature Reviews: Drug Discovery, 2, 2003, pp. 205-213.*
Definition of "alkylene"—Merriam-Webster Unabridged—http://unabridged.merriam-webster.com/cgi-bin/Third? book=Third & alkylene (Jan. 13, 2010).

* cited by examiner

*Primary Examiner*—Kamal A Saeed
*Assistant Examiner*—Valerie Rodriguez-Garcia
(74) *Attorney, Agent, or Firm*—Oona A. Manzari

(57) ABSTRACT

Macrocyclic compounds of formula (I), in which $B^1$ and $X^1$ taken together are alkylene which is unsubstituted or substituted with =O and having one $CH_2$ moiety unreplaced or replaced with CH=CH, O, NH or N(alkyl), which inhibit the activity of antiapoptotic Bcl-2 family protein members, compositions containing the compounds and methods of treating diseases during which are expressed one or more than one of an anti-apoptotic family protein member are disclosed.

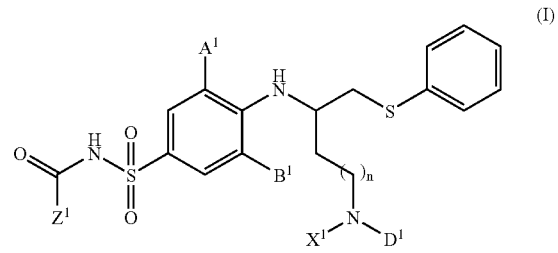

4 Claims, No Drawings

MACROCYCLIC INHIBITORS OF BCL PROTEINS

This application is a 371 of PCT/US06/19132 filed on May 17, 2006 which claims the benefit of U.S. Ser. No. 60/684,096 filed on May 24, 2005.

FIELD OF THE INVENTION

This invention pertains to compounds which inhibit the activity of anti-apoptotic Bcl-2 family protein members, compositions containing the compounds and methods of treating diseases during which are expressed one or more than one of an anti-apoptotic family protein member.

BACKGROUND OF THE INVENTION

Anti-apoptotic family protein members are associated with a number of diseases. There is therefore an existing need in the therapeutic arts for compounds which inhibit the activity of one of more than one of an anti-apoptotic family protein member.

SUMMARY OF THE INVENTION

One embodiment of this invention, therefore, pertains to compounds which inhibit the activity of one of more than one of an anti-apoptotic family protein member, the compounds having formula (I),

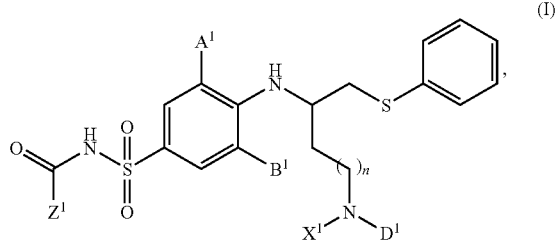

and therapeutically acceptable salts, prodrugs, salts of prodrugs and metabolites thereof, wherein $A^1$ is CN, $NO_2$, C(O)OH, F, Cl, Br, $CF_3$, $OCF_3$, $CF_2CF_3$, $OCF_2CF_3$, $C(O)R^1$, $C(O)OR^1$, $SR^1$, $C(O)NH_2$, $C(O)NHR^1$, $C(O)N(R^1)_2$, $NHS(O)R^1$, $SO_2NHR^1$, $S(O)R^1$, or $SO_2R^1$;

n is 1, 2 or 3;

$R^1$ is $R^2$, $R^3$, $R^4$ or $R^5$;

$R^2$ is alkyl, alkenyl or alkynyl;

$R^3$ is perhaloalkyl or perhaloalkenyl;

$R^4$ is $C_1$-alkyl(methyl) or $C_2$-alkenyl(vinyl), each of which is unsubstituted or substituted with one or two of independently selected F, Cl or Br;

$R^5$ is $C_2$-$C_6$-alkyl or $C_3$-$C_6$-alkenyl, each of which is unsubstituted or substituted with one or two or three or four of independently selected F, Cl or Br;

$B^1$ and $X^1$ are together and are alkylene, each of which is unsubstituted or substituted with (O) and each having one $CH_2$ moiety unreplaced or replaced with CHCH, O, NH or N(alkyl);

$D^1$ is H, alkyl or phenyl;

$Z^1$ is $Z^2$, $Z^3$ or $Z^4$;

$Z^2$ is phenyl or heteroaryl, each of which is substituted with $R^6$, $OR^6$, $SR^6$, $S(O)R^6$ or $SO_2R^6$;

$R^6$ is phenyl, heteroaryl cycloalkyl, cycloalkenyl, heterocycloalkyl or heterocycloalkenyl, each of which is unsubstituted or substituted with one or two of independently selected alkyl, spiroalkyl, F, Cl, Br, I, $R^7$, $OR^7$, $SR^7$, $S(O)R^7$, $SO_2R^7$;

$R^7$ is alkyl, alkenyl or alkynyl;

$Z^3$ is phenyl or heteroaryl, each of which is substituted with cycloalkyl, cycloalkenyl, heterocycloalkyl or heterocycloalkenyl, each of which is substituted with $CHR^8$;

$R^8$ is phenyl, heteroaryl cycloalkyl, cycloalkenyl, heterocycloalkyl or heterocycloalkenyl, each of which is unsubstituted or substituted with one or two or three of independently selected F, Cl, Br, I, OH, C(O)OH, C(O)$OCH_3$, CN, $NH_2$, $NH(CH_3)$, $N(CH_3)_2$, $CF_3$, $OCF_3$, $CF_2CF_3$ or $OCF_2CF_3$;

$Z^4$ is phenyl or heteroaryl, each of which is substituted with phenyl, heteroaryl cycloalkyl, cycloalkenyl, heterocycloalkyl or heterocycloalkenyl, each of which is substituted with one or two of $R^9$ or $OR^9$;

$R^9$ is alkyl, alkenyl or alkynyl, each of which is substituted with one or two of independently selected phenyl, heteroaryl cycloalkyl, cycloalkenyl, heterocycloalkyl or heterocycloalkenyl, each of which is unsubstituted or substituted with one or two or three of independently selected alkyl, alkenyl, alkynyl, F, Cl, Br, I, OH, C(O)OH, C(O)$OCH_3$, CN, $NH_2$, $NH(CH_3)$, $N(CH_3)_2$, $CF_3$, $OCF_3$, $CF_2CF_3$, $OCF_2CF_3$ or $R^{11}$;

$R^{11}$ is phenyl or heteroaryl, each of which is unsubstituted or substituted with one or two or three of F, Cl, Br, I, OH, C(O)OH, C(O)$OCH_3$, CN, $NH_2$, $NH(CH_3)$, $N(CH_3)_2$, $CF_3$, $OCF_3$, $CF_2CF_3$, $OCF_2CF_3$.

Another embodiment pertains to compounds having formula (I), and therapeutically acceptable salts, prodrugs, salts of prodrugs and metabolites thereof, wherein $A^1$ is $NO_2$;

n is 1, 2 or 3;

$B^1$ and $X^1$ are together and are alkylene, each of which is unsubstituted or substituted with (O) and each having one $CH_2$ moiety unreplaced or replaced with CHCH, O, NH or N(alkyl);

$D^1$ is H, alkyl or phenyl;

$Z^1$ is $Z^2$, $Z^3$ or $Z^4$;

$Z^2$ is phenyl substituted with $R^6$, $OR^6$, $SR^6$, $S(O)R^6$, or $SO_2R^6$;

$R^6$ is phenyl or heterocycloalkyl, each of which is unsubstituted or substituted with one or two of independently selected alkyl, spiroalkyl, F, Cl, Br or I;

$Z^3$ is phenyl substituted with heterocycloalkyl which is substituted with $CHR^8$;

$R^8$ is phenyl substituted with one or two or three of independently selected F, Cl, Br, I, OH, C(O)OH, C(O)$OCH_3$, CN, $NH_2$, $NH(CH_3)$, $N(CH_3)_2$, $CF_3$, $OCF_3$, $CF_2CF_3$ or $OCF_2CF_3$;

$Z^4$ is phenyl substituted with heterocycloalkyl which is substituted with one or two of $R^9$ or $OR^9$;

$R^9$ is alkyl or alkenyl, each of which is substituted with one or two of independently selected phenyl, cycloalkenyl or heterocycloalkenyl, each of which is unsubstituted or substituted with one or two or three of independently selected alkyl, alkenyl, alkynyl, F, Cl, Br, I, OH, C(O)OH, C(O)$OCH_3$, CN, $NH_2$, $NH(CH_3)$, $N(CH_3)_2$, $CF_3$, $OCF_3$, $CF_2CF_3$ or $R^{11}$;

$R^{11}$ is phenyl which is unsubstituted or substituted with one or two or three of F, Cl, Br, I, OH, C(O)OH C(O)$OCH_3$, CN, $NH_2$, $NH(CH_3)$, $N(CH_3)_2$, $CF_3$, $OCF_3$, $CF_2CF_3$, $OCF_2CF_3$.

Still another embodiment pertains to compounds having formula (I), and therapeutically acceptable salts, prodrugs, salts of prodrugs and metabolites thereof, wherein $A^1$ is $NO_2$;

n is 1;

$B^1$ and $X^1$ are together and are alkylene substituted with (O) and having one $CH_2$ moiety replaced with O;

$D^1$ is alkyl;

$Z^1$ is $Z^2$, $Z^3$ or $Z^4$;

$Z^2$ is phenyl substituted with $R^6$, $OR^6$;

$R^6$ is phenyl, piperidinyl or piperazinyl, each of which is unsubstituted or substituted with one or two of independently selected alkyl, spiroalkyl, F, Cl, Br or I;

$Z^3$ is phenyl substituted with heterocycloalkyl which is substituted with $CHR^8$;

$R^8$ is phenyl substituted with one or two or three of independently selected F, Cl, Br, I, $CF_3$ or $OCF_3$;

$Z^4$ is phenyl substituted with piperidinyl or piperazinyl, each of which is substituted with one or two of $R^9$ or $OR^9$;

$R^9$ is alkyl or alkenyl, each of which is substituted with one or two of independently selected phenyl, cycloalkenyl or heterocycloalkenyl, each of which is unsubstituted or substituted with one or two or three of independently selected alkyl, alkenyl, alkynyl, F, Cl, Br, I, OH, C(O)OH, $C(O)OCH_3$, CN, $NH_2$, $NH(CH_3)$, $N(CH_3)_2$, $CF_3$, $OCF_3$ or $R^{11}$;

$R^{11}$ is phenyl which is unsubstituted or substituted with one or two or three of F, Cl, Br, I, OH $CF_3$ or $OCF_3$.

Still another embodiment pertains to compounds having formula (I), and therapeutically acceptable salts, prodrugs, salts of prodrugs and metabolites thereof, wherein $A^1$ is $NO_2$; n is 1;

$B^1$ and $X^1$ are together and are $C_4$-alkylene substituted with (O) and having one $CH_2$ moiety replaced with O;

$D^1$ is $C_1$-alkyl(methyl);

$Z^1$ is $Z^2$, $Z^3$ or $Z^4$;

$Z^1$ is phenyl substituted with $R^6$, $OR^6$;

$R^6$ is phenyl, piperidinyl or piperazinyl, each of which is unsubstituted or substituted with one or two of independently selected $C_1$-alkyl, $C_4$-spiroalkyl, F, Cl, Br or I;

$Z^3$ is phenyl substituted with heterocycloalkyl which is substituted with $CHR^8$;

$R^8$ is phenyl substituted with $CF_3$;

$Z^4$ is phenyl substituted with piperidinyl or piperazinyl, each of which is substituted with one or two of $R^9$ or $OR^9$;

$R^9$ is $C_1$-alkyl or $C_2$-$C_3$-alkenyl, each of which is substituted with one or two of independently selected phenyl, $C_6$-$C_7$-cycloalkenyl or 5,6-dihydro-2H-pyranyl, each of which is unsubstituted or substituted with one or two or three of independently selected $C_1$-$C_2$-alkyl, F, Cl, Br, I, $CF_3$, or $R^{11}$;

$R^{11}$ is phenyl substituted with F, Cl, Br or I.

Still another embodiment pertains to compounds having formula (I), or therapeutically acceptable salts, prodrugs, salt of prodrugs or metabolites thereof, wherein $A^1$ is $NO_2$; n is 1; $B^1$ and $X^1$ together are $C(O)OCH_2CH_2$; $D^1$ is methyl; and $Z^1$ is 4-(4,4-dimethylpiperidin-1-yl)phenyl, 4-(4-((2-(4-chlorophenyl)-1-cyclohexen-1-yl)methyl)piperazin-1-yl)phenyl, 4-((4'-chloro(1,1'-biphen-2-ylmethyl)piperazin-1-yl)phenyl, 4-(8-azaspiro[4.5]dec-8-yl)phenyl, 4-(4-(2-(trifluoromethyl)benzylidene)piperidin-1-yl)phenyl or 4'-fluoro-1,1'-biphen-4-yl.

Still another embodiment pertains to compounds having formula (I), or therapeutically acceptable salts, prodrugs, salt of prodrugs or metabolites thereof, wherein $A^1$ is $NO_2$; n is 1; $B^1$ and $X^1$ together are $C(O)OCH_2CH_2$; $D^1$ is methyl; and $Z^1$ is 4-(4-methoxy-4-((Z)-2-phenylethenyl)piperidin-1-yl)phenyl, 4-(4-(2-fluorobenzyl)-4-methoxypiperidin-1-yl)phenyl, 4-((1,1'-biphen-2-ylmethyl)-4-methoxypiperidin-1-yl)phenyl, 4-(4-((2-(4-chlorophenyl)-4,4-dimethylcyclohex-1-en-1-yl)methyl)piperazin-1-yl)phenyl, 4-(4-((2-(4-chlorophenyl)cyclohept-1-en-1-yl)methyl)piperazin-1-yl)phenyl or 4-(4-(3,3-diphenyl-2-propenyl)piperazin-1-yl)phenyl.

Still another embodiment pertains to compounds having formula (I), or therapeutically acceptable salts, prodrugs, salt of prodrugs or metabolites thereof, wherein $A^1$ is $NO_2$; n is 1; $B^1$ and $X^1$ together are $C(O)OCH_2CH_2$; $D^1$ is methyl; and $Z^1$ is 4-(4-((1,1'-biphenyl)-2-ylmethyl)piperazin-1-yl)phenyl, 4-(4-(2-(trifluoromethyl)benzyl)piperazin-1-yl)phenyl, 4-(4-((2-(4-chlorophenyl)-4,4-diethylcyclohex-1-en-1-yl)methyl)piperazin-1-yl)phenyl, 4-(4-((4-(4-chlorophenyl)-5,6-dihydro-2H-pyran-3-yl)methyl)piperazin-1-yl)phenyl, 3-phenoxyphenyl or 4-(4-((2-(4-chlorophenyl)-1-cyclohexen-1-yl)methyl)piperazin-1-yl)phenyl.

Still another embodiment pertains to compounds having formula (I) which are (2R)-N-(4-(4,4-dimethylpiperidin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide, (2R)-N-(4-(4-((2-(4-chlorophenyl)-1-cyclohexen-1-yl)methyl)piperazin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide, (2R)-N-(4-(4-((4'-chloro(1,1'-biphenyl)-2-yl)methyl)piperazin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-1'-sulfonamide, (2R)-N-(4-(8-azaspiro[4.5]dec-8-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide, (2R)-5-methyl-13-nitro-9-oxo-2-((phenylsulfanyl)methyl)-N-(4-(4-(2-(trifluoromethyl)benzylidene)piperidin-1-yl)benzoyl)-1,2,3,4,5,6,7,9-octahydro-8,1,5-benzoxadiazacycloundecine-11-sulfonamide, (2R)-N-((4'-fluoro(1,1'-biphenyl)-4-yl)carbonyl)-5-methyl-13-nitro-9-oxo-2-((phenylsulfanyl)methyl)-1,2,3,4,5,6,7,9-octahydro-8,1,5-benzoxadiazacycloundecine-11-sulfonamide, (2R)-N-(4-(4-methoxy-4-((Z)-2-phenylethenyl)piperidin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-1'-sulfonamide, (2R)-N-(4-(4-(2-fluorobenzyl)-4-methoxypiperidin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide, (2R)-N-(4-(4-((1,1'-biphenyl)-2-ylmethyl)-4-methoxypiperidin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide, (2R)-N-(4-(4-((2-(4-chlorophenyl)-4,4-dimethylcyclohex-1-en-1-yl)methyl)piperazin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide, (2R)-N-(4-(4-((2-(4-chlorophenyl)cyclohept-1-en-1-yl)methyl)piperazin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide, (2R)-N-(4-(4-(3,3-diphenyl-2-propenyl)piperazin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide, (2R)-N-(4-(4-((1,1'-biphenyl)-2-ylmethyl)piperazin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-1'-sulfonamide, (2R)-5-methyl-13-nitro-9-oxo-2-((phenylsulfanyl)methyl)-N-(4-(4-(2-(trifluoromethyl)benzyl)piperazin-1-yl)benzoyl)-1,2,3,4,5,6,7,9-octahydro-8,1,5-benzoxadiazacycloundecine-1'-sulfonamide, (2R)-N-(4-(4-((2-(4-chlorophenyl)-4,4-diethylcyclohex-1-en-1-yl)methyl)piperazin-1-yl)benzoyl)-5-methyl-13-nitro-9-oxo-2-((phenylsulfanyl)methyl)-1,2,3,4,5,6,7,9-oc-tahydro-8,1,5-benzoxadiazacycloundecine-11-sulfonamide, (2R)-N-(4-(4-((4-(4-chlorophenyl)-5,6-dihydro-2H-pyran-3-yl)methyl)piperazin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide, (2R)-5-methyl-13-nitro-9-oxo-N-(3-phenoxybenzoyl)-2-((phenylsulfanyl)methyl)-1,2,3,4,5,6,7,9-octahydro-8,1,5-benzoxadiazacycloundecine-1,1-sulfonamide and (2R)-N-(4-(4-((2-(4-chlorophenyl)-1-cyclohexen-1-yl)methyl)piperazin-1-yl)benzoyl)-5-methyl-14-nitro-10-oxo-2-((phenylsulfanyl)methyl)-1,3,4,5,6,7,8,10-octahydro-2H-9,1,5-benzoxadiazacyclododecine-12-sulfonamide, and therapeutically acceptable salts, prodrugs, salt of prodrugs and metabolites thereof.

Still another embodiment pertains to compositions for treating diseases during which are expressed one or more than one of antiapoptotic Bcl-$X_L$ protein, antiapoptotic Bcl-2 protein or antiapoptotic Bcl-w protein, said compositions comprising an excipient and a therapeutically effective amount of a compound having formula (I).

Still another embodiment pertains to methods of treating diseases in a patient during which are expressed one or more than one of antiapoptotic Bcl-$X_L$ protein, antiapoptotic Bcl-2 protein or antiapoptotic Bcl-w protein, said methods comprising administering to the patient a therapeutically effective amount of a compound having formula (I).

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer and spleen cancer, said compositions comprising an excipient and a therapeutically effective amount of a compound having formula (I).

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer and spleen cancer in a patient, said methods comprising administering to the patient a therapeutically effective amount of a compound having formula (I).

Still another embodiment pertains to compositions for treating diseases in a patient during which is expressed one or more than one of antiapoptotic Bcl-$X_L$ protein, antiapoptotic Bcl-2 protein or antiapoptotic Bcl-w protein, said compositions comprising an excipient and a therapeutically effective amount of a compound having formula (I) and a therapeutically effective amount of one additional therapeutic agent or more than one additional therapeutic agent.

Still another embodiment pertains to methods of treating diseases in a patient during which is expressed one or more than one of antiapoptotic Bcl-$X_L$ protein, antiapoptotic Bcl-2 protein or antiapoptotic Bcl-w protein, said methods comprising administering to the patient a therapeutically effective amount of a compound having formula (I) and a therapeutically effective amount of one additional therapeutic agent or more than one additional therapeutic agent.

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer, said compositions comprising an excipient and a therapeutically effective amount of a compound having formula (I) and a therapeutically effective amount of one additional therapeutic agent or more than one additional therapeutic agent.

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer in a patient, said methods comprising administering to the patient a therapeutically effective amount of a compound having formula (I) and a therapeutically effective amount of one additional therapeutic agent or more than one additional therapeutic agent.

DETAILED DESCRIPTION OF THE INVENTION

Variable moieties of compounds herein are represented by identifiers (capital letters with numerical and/or alphabetical superscripts) and may be specifically embodied.

It is meant to be understood that proper valences are maintained for all moieties and combinations thereof, that monovalent moieties having more than one atom are attached through their left ends.

It is also meant to be understood that a specific embodiment of a variable moiety may be the same or different as another specific embodiment having the same identifier.

The term "cycloalkyl," as used herein, means $C_3$-cycloalkyl, $C_4$-cycloalkyl, $C_5$-cycloalkyl $C_6$-cycloalkyl, $C_7$-cycloalkyl, $C_8$-cycloalkyl, $C_9$-cycloalkyl and $C_{10}$-cycloalkyl.

The term "cycloalkenyl," as used herein, means $C_4$-cycloalkenyl, $C_5$-cycloalkenyl, $C_6$-cycloalkenyl, $C_7$-cycloalkenyl, $C_8$-cycloalkenyl, $C_9$-cycloalkenyl and $C_{10}$-cycloalkenyl.

The term "heteroaryl," as used herein, means furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl.

The term "heterocycloalkyl," as used herein, means cycloalkyl having one or two or three $CH_2$ moieties replaced with independently selected O, S, S(O), $SO_2$ or NH and one or two CH moieties unreplaced or replaced with N and also means cycloalkyl having one or two or three $CH_2$ moieties unreplaced or replaced with independently selected O, S, S(O), $SO_2$ or NH and one or two CH moieties replaced with N.

The term "heterocycloalkenyl," as used herein, means cycloalkenyl having one or two or three $CH_2$ moieties replaced with independently selected O, S, S(O), $SO_2$ or NH and one or two CH moieties unreplaced or replaced with N and also means cycloalkenyl having one or two or three $CH_2$ moieties unreplaced or replaced with independently selected O, S, S(O), $SO_2$ or NH and one or two CH moieties replaced with N.

The term "spiroalkyl," as used herein, means $C_2$-spiroalkyl, $C_3$-spiroalkyl, $C_4$-spiroalkyl, $C_5$-spiroalkyl and $C_6$-spiroalkyl.

The term "alkenyl," as used herein, means $C_2$-alkenyl, $C_3$-alkenyl, $C_4$-alkenyl, $C_5$-alkenyl and $C_6$-alkenyl.

The term "alkyl," as used herein, means $C_1$-alkyl, $C_2$-alkyl, $C_3$-alkyl, $C_4$-alkyl, $C_5$-alkyl and $C_6$-alkyl.

The term "alkynyl," as used herein, means $C_2$-alkynyl, $C_3$-alkynyl, $C_4$-alkynyl, $C_5$-alkynyl and $C_6$-alkynyl.

The term "$C_2$-alkenyl," as used herein, means ethenyl(vinyl).

The term "$C_3$-alkenyl," as used herein, means 1-propen-1-yl, 1-propen-2-yl (isopropenyl) and 1-propen-3-yl(allyl).

The term "$C_4$-alkenyl," as used herein, means 1-buten-1-yl, 1-buten-2-yl, 1,3-butadien-1-yl, 1,3-butadien-2-yl, 2-buten-1-yl, 2-buten-2-yl, 3-buten-1-yl, 3-buten-2-yl, 2-methyl-1-propen-1-yl and 2-methyl-2-propen-1-yl.

The term "$C_5$-alkenyl," as used herein, means 2-methylene-3-buten-1-yl, 2-methylenebut-1-yl, 2-methyl-1-buten-1-yl, 2-methyl-1,3-butadien-1-yl, 2-methyl-2-buten-1-yl, 2-methyl-3-buten-1-yl, 2-methyl-3-buten-2-yl, 3-methyl-1-buten-1-yl, 3-methyl-1-buten-2-yl, 3-methyl-1,3-butadien-1-yl, 3-methyl-1,3-butadien-2-yl, 3-methyl-2-buten-1-yl, 3-methyl-2-buten-2-yl, 3-methyl-3-buten-1-yl, 3-methyl-3-buten-2-yl, 1-penten-1-yl, 1-penten-2-yl, 1-penten-3-yl, 1,3-pentadien-1-yl, 1,3-penta-dien-2-yl, 1,3-pentadien-3-yl, 1,4-pentadien-1-yl, 1,4-pentadien-2-yl, 1,4-pentadien-3-yl, 2-penten-1-yl, 2-penten-2-yl, 2-penten-3-yl, 2,4-pentadien-1-yl, 2,4-pentadien-2-yl, 3-penten-1-yl, 3-penten-2-yl, 4-penten-1-yl and 4-penten-2-yl.

The term "$C_6$-alkenyl," as used herein, means 2,2-dimethyl-3-buten-1-yl, 2,3-dimethyl-1-buten-1-yl, 2,3-dimethyl-1,3-butadien-1-yl, 2,3-dimethyl-2-buten-1-yl, 2,3-dimethyl-3-buten-1-yl, 2,3-dimethyl-3-buten-2-yl, 3,3-dimethyl-1-buten-1-yl, 3,3-dimethyl-1-buten-2-yl, 2-ethenyl-1,3-butadien-1-yl, 2-ethenyl-2-buten-1-yl, 2-ethyl-1-buten-1-yl, 2-ethyl-1,3-butadien-1-yl, 2-ethyl-2-buten-1-yl, 2-ethyl-3-buten-1-yl, 1-hexen-1-yl, 1-hexen-2-yl, 1-hexen-3-yl, 1,3-hexadien-1-yl, 1,3-hexadien-2-yl, 1,3-hexadien-3-yl, 1,3,5-hexatrien-1-yl, 1,3,5-hexatrien-2-yl, 1,3,5-hexatrien-3-yl, 1,4-hexadien-1-yl, 1,4-hexadien-2-yl, 1,4-hexadien-3-yl, 1,5-hexadien-1-yl, 1,5-hexadien-2-yl, 1,5-hexadien-3-yl, 2-hexen-1-yl, 2-hexen-2-yl, 2-hexen-3-yl, 2,4-hexadien-1-yl, 2,4-hexadien-2-yl, 2,4-hexadien-3-yl, 2,5-hexadien-1-yl, 2,5-hexadien-2-yl, 2,5-hexadien-3-yl, 3-hexen-1-yl, 3-hexen-2-yl, 3-hexen-3-yl, 3,5-hexadien-1-yl, 3,5-hexadien-2-yl, 3,5-hexadien-3-yl, 4-hexen-1-yl, 4-hexen-2-yl, 4-hexen-3-yl, 5-hexen-1-yl, 5-hexen-2-yl, 5-hexen-3-yl, 2-methylene-3-methyl-3-buten-1-yl, 2-methylene-3-methylbut-1-yl, 2-methylene-3-penten-1-yl, 2-methylene-4-penten-1-yl, 2-methylenepent-1-yl, 2-methylenepent-3-yl, 3-methylene-1-penten-1-yl, 3-methylene-1-penten-2-yl, 3-methylenepent-1-yl, 3-methylene-1,4-pentadien-1-yl, 3-methylene-1,4-pentadien-2-yl, 3-methylene-pent-2-yl, 2-methyl-1-penten-1-yl, 2-methyl-1-penten-3-yl, 2-methyl-1,3-pentadien-1-yl, 2-methyl-1,3-pentadien-3-yl, 2-methyl-1,4-pentadien-1-yl, 2-methyl-1,4-pentadien-3-yl, 2-methyl-2-penten-1-yl, 2-methyl-2-penten-3-yl, 2-methyl-2,4-pentadien-1-yl, 2-methyl-2,4-pentadien-3-yl, 2-methyl-3-penten-1-yl, 2-methyl-3-penten-2-yl, 2-methyl-3-penten-3-yl, 2-methyl-4-penten-1-yl, 2-methyl-4-penten-2-yl, 2-methyl-4-penten-3-yl, 3-methyl-1-penten-1-yl, 3-methyl-1-penten-2-yl, 3-methyl-1,3-pentadien-1-yl, 3-methyl-1,3-pentadien-2-yl, 3-methyl-1,4-pentadien-1-yl, 3-methyl-1,4-pentadien-3-yl, 3-methyl-2-penten-1-yl, 3-methyl-2-penten-2-yl, 3-methyl-2,4-pentadien-1-yl, 3-methyl-3-penten-1-yl, 3-methyl-3-penten-2-yl, 3-methyl-4-penten-1-yl, 3-methyl-4-penten-2-yl, 3-methyl-4-penten-3-yl, 4-methyl-1-penten-1-yl, 4-methyl-1-penten-2-yl, 4-methyl-1-penten-3-yl, 4-methyl-1,3-pentadien-1-yl, 4-methyl-1,3-pentadien-2-yl, 4-methyl-1,3-pentadien-3-yl, 4-methyl-1,4-pentadien-1-yl, 4-methyl-1,4-pentadien-2-yl, 4-methyl-1,4-pentadien-3-yl, 4-methylene-2-penten-3-yl, 4-methyl-2-penten-1-yl, 4-methyl-2-penten-2-yl, 4-methyl-2-penten-3-yl, 4-methyl-2,4-pentadien-1-yl, 4-methyl-2,4-pentadien-2-yl, 4-methyl-3-penten-1-yl, 4-methyl-3-penten-2-yl, 4-methyl-3-penten-3-yl, 4-methyl-4-penten-1-yl and 4-methyl-4-penten-2-yl.

The term "$C_1$-alkyl," as used herein, means methyl.

The term "$C_2$-alkyl," as used herein, means ethyl.

The term "$C_3$-alkyl," as used herein, means prop-1-yl and prop-2-yl(isopropyl).

The term "$C_4$-alkyl," as used herein, means but-1-yl, but-2-yl, 2-methylprop-1-yl and 2-methylprop-2-yl(tert-butyl).

The term "$C_5$-alkyl," as used herein, means 2,2-dimethylprop-1-yl(neo-pentyl), 2-methylbut-1-yl, 2-methylbut-2-yl, 3-methylbut-1-yl, 3-methylbut-2-yl, pent-1-yl, pent-2-yl and pent-3-yl.

The term "$C_6$-alkyl," as used herein, means 2,2-dimethylbut-1-yl, 2,3-dimethylbut-1-yl, 2,3-dimethylbut-2-yl, 3,3-dimethylbut-1-yl, 3,3-dimethylbut-2-yl, 2-ethylbut-1-yl, hex-1-yl, hex-2-yl, hex-3-yl, 2-methylpent-1-yl, 2-methylpent-2-yl, 2-methylpent-3-yl, 3-methylpent-1-yl, 3-methylpent-2-yl, 3-methylpent-3-yl, 4-methylpent-1-yl and 4-methylpent-2-yl.

The term "alkylene," as used herein, means $C_3$-alkylene, $C_4$-alkylene, $C_5$-alkylene and $C_6$-alkylene.

The term "$C_3$-alkylene," as used herein, means propyl-1,3-ene, the ends of which are attached to different atoms.

The term "$C_4$-alkylene," as used herein, means butyl-1,4-ene, the ends of which are attached to different atoms.

The term "$C_5$-alkylene," as used herein, means pentyl-1,5-ene, the ends of which are attached to different atoms.

The term "$C_6$-alkylene," as used herein, means hexyl-1,6-ene, the ends of which are attached to different atoms.

The term "$C_2$-alkynyl," as used herein, means ethynyl (acetylenyl).

The term "$C_3$-alkynyl," as used herein, means 1-propyn-1-yl and 2-propyn-1-yl (propargyl).

The term "$C_4$-alkynyl," as used herein, means 1-butyn-1-yl, 1,3-butadiyn-1-yl, 2-butyn-1-yl, 3-butyn-1-yl and 3-butyn-2-yl.

The term "$C_5$-alkynyl," as used herein, means 2-methyl-3-butyn-1-yl, 2-methyl-3-butyn-2-yl, 3-methyl-1-butyn-1-yl, 1,3-pentadiyn-1-yl, 1,4-pentadiyn-1-yl, 1,4-pentadiyn-3-yl, 2,4-pentadiyn-1-yl, 1-pentyn-1-yl, 1-pentyn-3-yl, 2-pentyn-1-yl, 3-pentyn-1-yl, 3-pentyn-2-yl, 4-pentyn-1-yl and 4-pentyn-2-yl.

The term "$C_6$-alkynyl," as used herein, means 2,2-dimethyl-3-butyn-1-yl, 3,3-dimethyl-1-butyn-1-yl, 2-ethyl-3-butyn-1-yl, 2-ethynyl-3-butyn-1-yl, 1-hexyn-1-yl, 1-hexyn-3-yl, 1,3-hexadiyn-1-yl, 1,3,5-hexatriyn-1-yl, 1,4-hexadiyn-1-yl, 1,4-hexadiyn-3-yl, 1,5-hexadiyn-1-yl, 1,5-hexadiyn-3-yl, 2-hexyn-1-yl, 2,5-hexadiyn-1-yl, 3-hexyn-1-yl, 3-hexyn-2-yl, 3,5-hexadiyn-2-yl, 4-hexyn-1-yl, 4-hexyn-2-yl, 4-hexyn-3-yl, 5-hexyn-1-yl, 5-hexyn-2-yl, 5-hexyn-3-yl, 2-methyl-3-pentyn-1-yl, 2-methyl-3-pentyn-2-yl, 2-methyl-4-pentyn-1-yl, 2-methyl-4-pentyn-2-yl, 2-methyl-4-pentyn-3-yl, 3-methyl-1-pentyn-1-yl, 3-methyl-4-pentyn-1-yl, 3-methyl-4-pentyn-2-yl, 3-methyl-1,4-pentadiyn-1-yl, 3-methyl-1,4-pentadiyn-3-yl, 3-methyl-4-pentyn-1-yl, 3-methyl-4-pentyn-3-yl, 4-methyl-1-pentyn-1-yl and 4-methyl-2-pentyn-1-yl.

The term "$C_3$-cycloalkenyl," as used herein, means cycloprop-1-en-1-yl and cycloprop-2-en-1-yl.

The term "C₄-cycloalkenyl," as used herein, means cyclobut-1-en-1-yl and cyclobut-2-en-1-yl.

The term "C₅-cycloalkenyl," as used herein, means cyclopent-1-en-1-yl, cyclopent-2-en-1-yl, cyclopent-3-en-1-yl and cyclopenta-1,3-dien-1-yl.

The term "C₆-cycloalkenyl," as used herein, means cyclohex-1-en-1-yl, cyclohex-2-en-1-yl, cyclohex-3-en-1-yl, cyclohexa-1,3-dien-1-yl, cyclohexa-1,4-dien-1-yl, cyclohexa-1,5-dien-1-yl, cyclohexa-2,4-dien-1-yl and cyclohexa-2,5-dien-1-yl.

The term "C₇-cycloalkenyl," as used herein, means bicyclo[2.2.1]hept-2-en-1-yl, bicyclo[2.2.1]hept-2-en-2-yl, bicyclo[2.2.1]hept-2-en-5-yl, bicyclo[2.2.1]hept-2-en-7-yl, bicyclo[2.2.1]hepta-2,5-dien-1-yl, bicyclo[2.2.1]hepta-2,5-dien-2-yl, bicyclo[2.2.1]hepta-2,5-dien-7-yl, cyclohept-1-en-1-yl, cyclohept-2-en-1-yl, cyclohept-3-en-1-yl, cyclohept-4-en-1-yl, cyclohepta-1,3-dien-1-yl, cyclohepta-1,4-dien-1-yl, cyclohepta-1,5-dien-1-yl, cyclohepta-1,6-dien-1-yl, cyclohepta-2,4-dien-1-yl, cyclohepta-2,5-dien-1-yl, cyclohepta-2,6-dien-1-yl, cyclohepta-3,5-dien-1-yl, cyclohepta-1,3,5-trien-1-yl, cyclohepta-1,3,6-trien-1-yl, cyclohepta-1,4,6-trien-1-yl and cyclohepta-2,4,6-trien-1-yl.

The term "C₉-cycloalkenyl," as used herein, means bicyclo[2.2.2]oct-2-en-1-yl, bicyclo[2.2.2]oct-2-en-2-yl, bicyclo[2.2.2]oct-2-en-5-yl, bicyclo[2.2.2]oct-2-en-7-yl, bicyclo[2.2.2]octa-2,5-dien-1-yl, bicyclo[2.2.2]octa-2,5-dien-2-yl, bicyclo[2.2.2]octa-2,5-dien-7-yl, bicyclo[2.2.2]octa-2,5,7-trien-1-yl, bicyclo[2.2.2]octa-2,5,7-trien-2-yl cyclooct-1-en-1-yl, cyclooct-2-en-1-yl, cyclooct-3-en-1-yl, cyclooct-4-en-1-yl, cycloocta-1,3-dien-1-yl, cycloocta-1,4-dien-1-yl, cycloocta-1,5-dien-1-yl, cycloocta-1,6-dien-1-yl, cycloocta1,7-dien-1-yl, cycloocta-2,4-dien-1-yl, cycloocta-2,5-dien-1-yl, cycloocta-2,6-dien-1-yl, cycloocta-2,7-dien-1-yl, cycloocta-3,5-dien-1-yl, cycloocta-3,6-dien-1-yl, cycloocta-1,3,5-trien-1-yl, cycloocta-1,3,6-trien-1-yl, cycloocta-1,3,7-trien-1-yl, cycloocta-1,4,6-trien-1-yl, cycloocta-1,4,7-trien-1-yl, cycloocta-1,5,7-trien-1-yl, cycloocta-2,4,6-trien-1-yl, cycloocta-2,4,7-trien-1-yl, cycloocta-2,5,7-trien-1-yl and cycloocta-1,3,5,7-tetraen-1-yl.

The term "C₉-cycloalkenyl," as used herein, means cyclonon-1-en-1-yl, cyclonon-2-en-1-yl, cyclonon-3-en-1-yl, cyclonon-4-en-1-yl, cyclonon-5-en-1-yl, cyclonona-1,3-dien-1-yl, cyclonona-1,4-dien-1-yl, cyclonona-1,5-dien-1-yl, cyclonona-1,6-dien-1-yl, cyclonona-1,7-dien-1-yl, cyclonona-1,8-dien-1-yl, cyclonona-2,4-dien-1-yl, cyclonona-2,5-dien-1-yl, cyclonona-2,6-dien-1-yl, cyclonona-2,7-dien-1-yl, cyclonona-2,8-dien-1-yl, cyclonona-3,5-dien-1-yl, cyclonona-3,6-dien-1-yl, cyclonona-3,7-dien-1-yl, cyclonona-4,6-dien-1-yl, cyclonona-1,3,5-trien-1-yl, cyclonona-1,3,6-trien-1-yl, cyclonona-1,3,7-trien-1-yl, cyclonona-1,3,8-trien-1-yl, cyclonona-1,4,6-trien-1-yl, cyclonona-1,4,7-trien-1-yl, cyclonona-1,4,8-trien-1-yl, cyclonona-1,5,7-trien-1-yl, cyclonona-1,5,8-trien-1-yl, cyclonona-1,6,8-trien-1-yl, cyclonona-2,4,8-trien-1-yl, cyclonona-2,4,6-trien-1-yl, cyclonona-2,4,7-trien-1-yl, cyclonona-2,4,8-trien-1-yl, cyclonona-2,5,7-trien-1-yl, cyclonona-2,5,8-trien-1-yl, cyclonona-1,3,5,7-tetraen-1-yl, cyclonona-1,3,5,8-tetraen-1-yl, cyclonona-1,3,6,8-tetraen-1-yl, cyclonona-1,4,6,8-tetraen-1-yl and cyclonona-2,4,6,8-tetraen-1-yl.

The term "C₁₀-cycloalkenyl," as used herein, means cyclodec-1-en-1-yl, cyclodec-2-en-1-yl, cyclodec-3-en-1-yl, cyclodec-4-en-1-yl, cyclodec-5-en-1-yl, cyclodeca-1,3-dien-1-yl, cyclodeca-1,4-dien-1-yl, cyclodeca-1,5-dien-1-yl, cyclodeca-1,6-dien-1-yl, cyclodeca-1,7-dien-1-yl, cyclodeca-1,8-dien-1-yl, cyclodeca-1,9-dien-1-yl, cyclodeca-2,4-dien-1-yl, cyclodeca-2,5-dien-1-yl, cyclodeca-2,6-dien-1-yl, cyclodeca-2,7-dien-1-yl, cyclodeca-2,8-dien-1-yl, cyclodeca-2,9-dien-1-yl, cyclodeca-3,5-dien-1-yl, cyclodeca-3,6-dien-1-yl, cyclodeca-3,7-dien-1-yl, cyclodeca-3,8-dien-1-yl, cyclodeca-4,6-dien-1-yl, cyclodeca-4,7-dien-1-yl, cyclodeca-1,3,5-trien-1-yl, cyclodeca-1,3,6-trien-1-yl, cyclodeca-1,3,7-trien-1-yl, cyclodeca-1,3,8-trien-1-yl, cyclodeca-1,3,9-trien-1-yl, cyclodeca-1,4,6-trien-1-yl, cyclodeca-1,4,7-trien-1-yl, cyclodeca-1,4,8-trien-1-yl, cyclodeca-1,4,9-trien-1-yl, cyclodeca-1,5,7-trien-1-yl, cyclodeca-1,5,8-trien-1-yl, cyclodeca-1,5,9-trien-1-yl, cyclodeca-1,6,8-trien-1-yl, cyclodeca-1,6,9-trien-1-yl, cyclodeca-1,7,9-trien-1-yl, cyclodeca-2,4,6-trien-1-yl, cyclodeca-2,4,7-trien-1-yl, cyclodeca-2,4,8-trien-1-yl, cyclodeca-2,4,9-trien-1-yl, cyclodeca-2,5,7-trien-1-yl, cyclodeca-2,5,8-trien-1-yl, cyclodeca-2,5,9-trien-1-yl, cyclodeca-2,6,8-trien-1-yl, cyclodeca-3,5,7-trien-1-yl, cyclodeca-3,5,8-trien-1-yl, cyclodeca-1,3,5,7-tetraen-1-yl, cyclodeca-1,3,5,8-tetraen-1-yl, cyclodeca-1,3,5,9-tetraen-1-yl, cyclodeca-1,3,6,8-tetraen-1-yl, cyclodeca-1,3,6,9-tetraen-1-yl, cyclodeca-1,3,7,9-tetraen-1-yl, cyclodeca-1,4,6,8-tetraen-1-yl, cyclodeca-1,4,6,9-tetraen-1-yl, cyclodeca-1,4,7,9-tetraen-1-yl, cyclodeca-1,5,7,9-tetraen-1-yl, cyclodeca-2,4,6,8-tetraen-1-yl, cyclodeca-2,4,6,9-tetraen-1-yl, cyclodeca-2,4,7,9-tetraen-1-yl and cyclodeca-1,3,5,7,9-pentaen-1-yl.

The term "C₃-cycloalkyl," as used herein, means cycloprop-1-yl.

The term "C₄-cycloalkyl," as used herein, means cyclobut-1-yl.

The term "C₅-cycloalkyl," as used herein, means cyclopent-1-yl.

The term "C₆-cycloalkyl," as used herein, means cyclohex-1-yl.

The term "C₇-cycloalkyl," as used herein, means bicyclo[2.2.1]hept-1-yl, bicyclo[2.2.1]hept-2-yl, bicyclo[2.2.1]hept-7-yl and cyclohept-1-yl.

The term "C₈-cycloalkyl," as used herein, means bicyclo[2.2.2]oct-1-yl, bicyclo[2.2.2]oct-2-yl, bicyclo[2.2.2]oct-7-yl bicyclo[3.2.1]oct-1-yl, bicyclo[3.2.1]oct-2-yl, bicyclo[3.2.1]oct-3-yl, bicyclo[3.2.1]oct-6-yl, bicyclo[3.2.1]oct-8-yl and cyclooct-1-yl.

The term "C₉-cycloalkyl," as used herein, means bicyclo[3.3.1]non-1-yl, bicyclo[3.3.1]non-2-yl, bicyclo[3.3.1]non-3-yl, bicyclo[3.3.1]non-9-yl and cyclonon-1-yl.

The term "C₁₀-cycloalkyl," as used herein, means adamant-1-yl, adamant-2-yl and cyclodec-1-yl.

The term "perhaloalkyl," as used herein, means $C_1$-perhaloalkyl, $C_2$-perhaloalkyl, $C_3$-perhaloalkyl, $C_4$-perhaloalkyl, $C_5$-perhaloalkyl and $C_6$-perhaloalkyl. The term "$C_1$-perhaloalkyl," as used herein, means $C_1$-alkyl, each of the hydrogen atoms thereof having been replaced by independently selected F, Cl or Br atoms.

The term "$C_2$-perhaloalkyl," as used herein, means $C_2$-alkyl, each of the hydrogen atoms thereof having been replaced by independently selected F, Cl or Br atoms.

The term "$C_3$-perhaloalkyl," as used herein, means $C_3$-alkyl, each of the hydrogen atoms thereof having been replaced by independently selected F, Cl or Br atoms.

The term "$C_4$-perhaloalkyl," as used herein, means $C_4$-alkyl, each of the hydrogen atoms thereof having been replaced by independently selected F, Cl or Br atoms.

The term "$C_5$-perhaloalkyl," as used herein, means $C_5$-alkyl, each of the hydrogen atoms thereof having been replaced by independently selected F, Cl or Br atoms.

The term "$C_6$-perhaloalkyl," as used herein, means $C_6$-alkyl, each of the hydrogen atoms thereof having been replaced by independently selected F, Cl or Br atoms.

The term "$C_2$-spiroalkyl," as used herein, means eth-1,2-ylene, both ends of which are attached to the same carbon of a $CH_2$ moiety by replacement of the hydrogen atoms thereof.

The term "$C_3$-spiroalkyl," as used herein, means prop-1,3-ylene, both ends of which are attached to the same carbon of a $CH_2$ moiety by replacement of the hydrogen atoms thereof.

The term "$C_4$-spiroalkyl," as used herein, means but-1,4-ylene, both ends of which are attached to the same carbon of a $CH_2$ moiety by replacement of the hydrogen atoms thereof.

The term "$C_5$-spiroalkyl," as used herein, means pent-1,5-ylene, both ends of which are attached to the same carbon of a $CH_2$ moiety by replacement of the hydrogen atoms thereof.

The term "$C_6$-spiroalkyl," as used herein, means hex-1,6-ylene, both ends of which are attached to the same carbon of a $CH_2$ moiety by replacement of the hydrogen atoms thereof.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds of this invention may also exist as a mixture of "Z" and "E" isomers.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like.

Compounds of this invention containing NH, C(O)OH, OH or SH moieties may have attached thereto prodrug-forming moieties. The prodrug-forming moieties are removed by metabolic processes and release the compounds having the freed NH, C(O)OH, OH or SH in vivo. Prodrugs are useful for adjusting such pharmacokinetic properties of the compounds as solubility and/or hydrophobicity, absorption in the gastrointestinal tract, bioavailability, tissue penetration, and rate of clearance.

Metabolites of compounds having formula (I), produced by in vitro or in vivo metabolic processes, may also have utility for treating diseases associated with expression of an anti-apoptotic family protein member such as of BCl-$X_L$ protein, Bcl-2 protein or Bcl-w protein.

Certain precursor compounds which may be metabolized in vitro or in vivo to form compounds having formula (I) may also have utility for treating diseases associated with expression of an anti-apoptotic family protein member such as of BCl-$X_L$ protein, Bcl-2 protein or Bcl-w protein.

Compounds having formula (I) may exist as acid addition salts, basic addition salts or zwitterions. Salts of compounds having formula (I) are prepared during their isolation or following their purification. Acid addition salts are those derived from the reaction of a compound having formula (I) with acid. Accordingly, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds having formula (I) are meant to be embraced by this invention. Basic addition salts of compounds are those derived from, the reaction of the compounds having formula (I) with the bicarbonate, carbonate, hydroxide or phosphate of cations such as lithium, sodium, potassium, calcium and magnesium.

Compounds having formula (I) may be administered, for example, bucally, ophthalmically, orally, osmotically, parenterally (intramuscularly, intraperintoneally intrasternally, intravenously, subcutaneously), rectally, topically, transdermally and vaginally.

Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

Compounds having formula (I) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (I) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

Compounds having formula (I) may be administered with one or more than one additional therapeutic agents, wherein additional therapeutic agents include radiation or chemotherapeutic agents, wherein chemotherapeutic agents include, but are not limited to, carboplatin, cisplatin, cyclophosphamide, dacarbazine, dexamethasone, docetaxel, doxorubicin, etoposide, fludarabine, irinotecan, CHOP (C: Cytoxan® (cyclophosphamide); H: Adriamycin® (hydroxydoxorubicin); O: Vincristine (Oncovin®); P: prednisone), paclitaxel, rapamycin, Rituxin® (rituximab), vincristine and the like.

BAX and BAD peptides are reported in Zhang, H. C., Nimmer, P., Rosenberg, S. H., Ng, S. C., and Joseph, M. (2002). Development of a High-Throughput Fluorescence Polarization Assay for Bcl-$X_L$. Analytical Biochemistry 307, 70-75.

Binding affinity of compounds having formula (I) to Bcl-$X_L$ protein is indicia of their inhibition of the activity of this protein. To determine the binding affinity of compounds having formula (I) to Bcl-$X_L$ protein, representative examples were diluted in DMSO to concentrations between 100 μM and 1 μM and added to each well of a 96-well microtiter plate. A mixture comprising 125 L per well of assay buffer (20 mM phosphate buffer (pH 7.4), 1 mM EDTA, 50 mM NaCl, 0.05% PF-68), 6 nM of BCl-$X_L$ protein (prepared as described in Science 1997, 275, 983-986), 1 nM fluorescein-labeled BAD peptide (prepared in-house) and the DMSO solution of the compound was shaken for 2 minutes and placed in a LJL Analyst (LJL Bio Systems, CA). A negative control (DMSO, 15 nM BAD peptide, assay buffer) and a positive control (DMSO, 1 nM BAD peptide, 6 rAM Bcl-$X_L$, assay buffer) were used to determine the range of the assay. Polarization was measured at room temperature using a continuous Fluorescein lamp (excitation 485 nm, emission 530 nm). Percentage of inhibition was determined by (1-((mP value of well-negative control)/range))×100%. $K_i$ values, calculated using Microsoft Excel, were <1.0 nM, <1.0 nM, <1.0 nM, <1.0 nM, <1.0 nM, <1.0 nM, <1.0 nM, <1.0 nM, <1.0 nM, <1.0 nM, <1.0 nM, 1.2 nM, 2.0 nM, 2.5 nM, 5.8 nM, 9.2 nM and 227 nM.

Binding affinity of compounds having formula (I) to Bcl-2 protein is indicia of their inhibition of the activity of this protein. To determine the binding affinity of compounds having formula (I) to Bcl-2, representative examples were diluted in DMSO to concentrations between 10 μM and 10 μM and added to each well of a 96-well microtiter plate. A mixture comprising 125 L per well of assay buffer (20 mM phosphate buffer (pH 7.4), 1 mM EDTA, 50 mM NaCl, 0.05% PF-68), 10 nM of Bcl-2 protein (prepared according to the procedure described in PNAS 2001, 98, 3012-3017), 1 nM fluorescein-labeled BAX peptide (prepared in-house) and the DMSO solution of the representative example was shaken for 2 minutes and placed in a LJL Analyst (LJL Bio Systems, CA. Polarization was measured at room temperature using a continuous Fluorescein lamp (excitation 485 nm, emission 530 nm). Ki values, calculated using Microsoft Excel, were <1.0 nM, <1.0 nM, <1.0 nM, <1.0 nM, <1.0 nM, <1.0 nM, <1.0 nM, <1.0 nM, <1.0 nM, <1.0 nM, <1.0 nM, 3.5 nM, 14.4 nM, 16.1 nM, 31.2 nM and 893 nM.

These data demonstrate the utility of compounds having formula (I) as binders to and inhibitors of anti-apoptotic BCl-$X_L$ protein and anti-apoptotic Bcl-2.

It is expected that, because compounds having formula (I) bind to and inhibit the activity of BCl-$X_L$ and Bcl-2, they would also have utility as inhibitors of anti-apoptotic family protein members having close structural homology to BCl-$X_L$ and Bcl-2 such as, for example, anti-apoptotic Bcl-w protein.

Accordingly, compounds having formula (I) are expected to have utility in treatment of diseases during which anti-apoptotic Bcl-$X_L$ protein, anti-apoptotic Bcl-2 protein, anti-apoptotic Bcl-w protein or a combination thereof, are expressed.

Diseases during which anti-apoptotic Bcl-$X_L$ protein, anti-apoptotic Bcl-2 protein, anti-apoptotic Bcl-w protein or a combination thereof, are expressed include, but are not limited to cancer and autoimmune disorders, wherein cancer includes, but is not limited to, bladder cancer, brain cancer, breast cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer and small cell lung cancer (commonly-owned U.S. patent application Ser. No. 10/988,338, Cancer Res., 2000, 60, 6101-10); autoimmune disorders include, but are not limited to, acquired immunodeficiency disease syndrome, autoimmune lymphoproliferative syndrome, hemolytic anemia, inflammatory diseases, and thrombocytopenia (Current Allergy and Asthma Reports 2003, 3:378-384; Br. J. Haematol. 2000 September; 110(3): 584-90; Blood 2000 Feb. 15; 95(4): 1283-92; and New England Journal of Medicine 2004 September; 351(14): 1409-1418).

Compounds having formula (I) may be made by synthetic chemical processes, examples of which are shown hereinbelow. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl(phenylmethyl), benzylidene, benzyloxycarbonyl(Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl(Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphino)ethoxycarbonyl and the like.

The following abbreviations have the meanings indicated. CDI means carbonyldiimidazole; DIBAL means diisobutylaluminum hydride; DIEA means diisopropylethylamine; DMAP means N,N-dimethylaminopyridine; DMSO means dimethylsulfoxide; EDAC means 1-(3-dimethylaminopropyl)-3-ethylcarbodiimide; HATU means O-(7-azabenzotriazol-1-yl)-N,N'N'N'-tetramethyluronium PyBOP means benzotriazol-1-yloxytripyrrolidinophosphonium hexafluorophosphate; TEA means triethylamine; TFA means trifluoroacetic acid; THF means tetrahydrofuran and PPh$_3$ means triphenylphosphine.

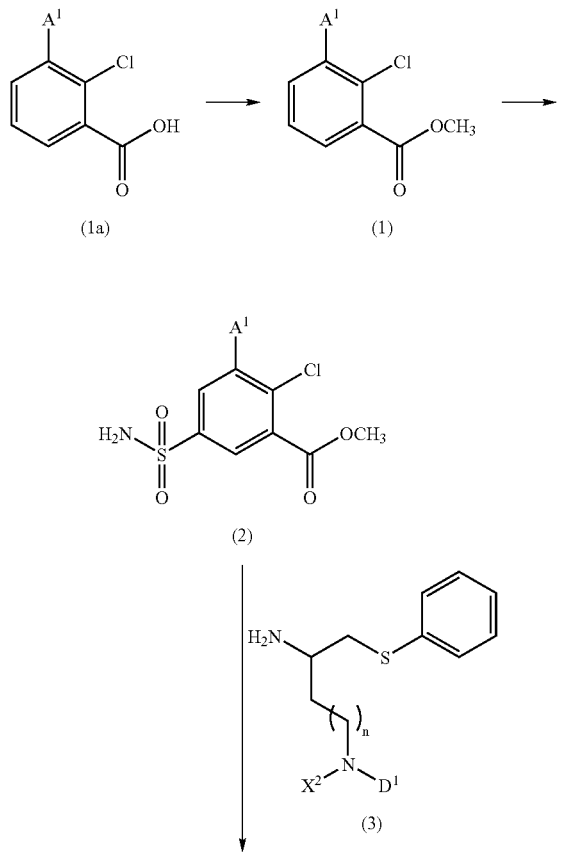

SCHEME 1

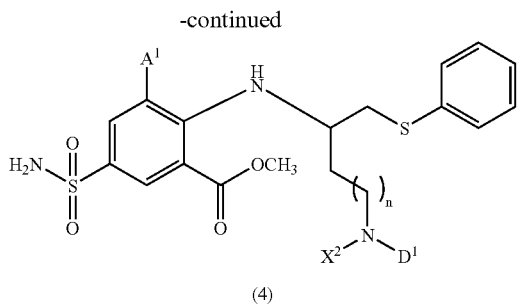

(4)

As shown in SCHEME 1, compounds having formula (1a) may be converted to compounds having formula (1) by reacting the former, methanol and hydrogen chloride. Compounds having formula (1) may be converted to compounds having formula (2) by reacting the former, chlorosulfonic acid, and ammonia.

Compounds having formula (2) may be converted to compounds having formula (4) by reacting the former, compounds having formula (3) and a DIEA.

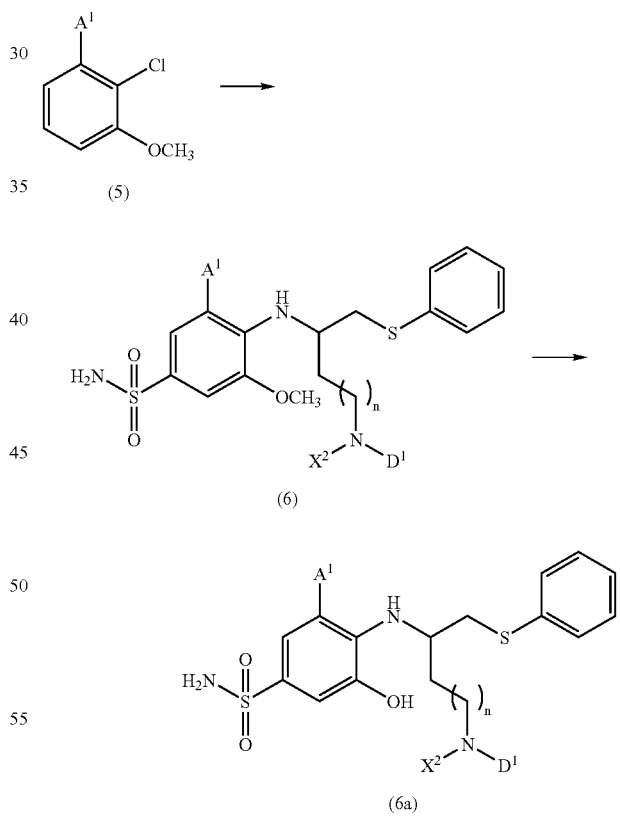

SCHEME 2

As shown in SCHEME 2, compounds having formula (5) may be converted to compounds having formula (6) by the chemistry used to convert compounds having formula (1) to compounds having formula (4) in SCHEME 1. Compounds having formula (6) may be converted to compounds having formula (6a) by reacting the former and $CH_3CH_2S^-Na^+$.

SCHEME 3

(4) ⟶

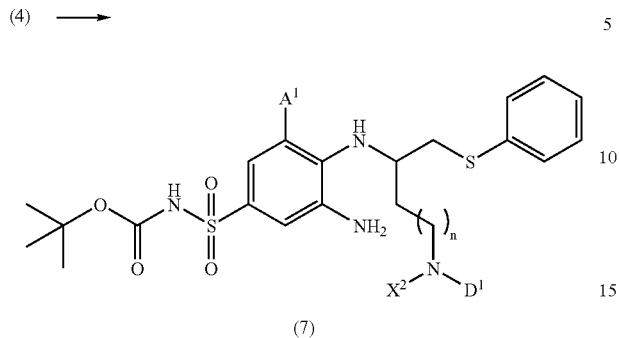

(7)

As shown in SCHEME 3, compounds having formula (4) may be converted to compounds having formula (7) by reacting the former and di(tert-butyl)dicarbonate followed by DPPA and DIEA to provide an isocyanate intermediate which may then be hydrolyzed with water to provide compounds having formula (7).

SCHEME 4

(4) ⟶

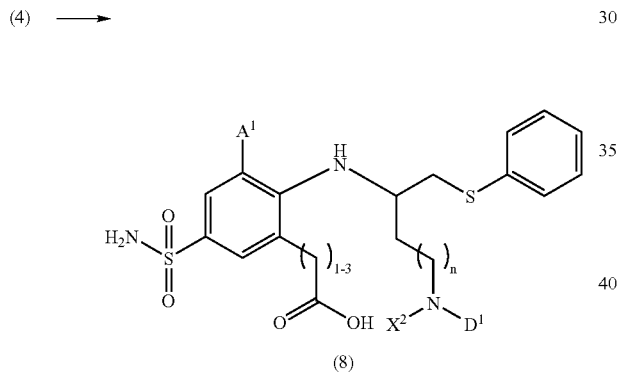

(8)

As shown in SCHEME 4, compounds having formula (4) may be converted to compounds having formula (8) by reacting the former and lithium hydroxide, then diazomethane then silver (I) oxide to provide compounds having formula (8). This procedure may be repeated, as necessary, to provide other homologues.

SCHEME 5

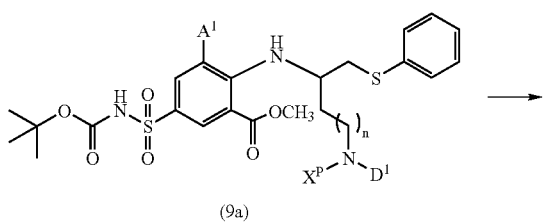

(9a)

-continued

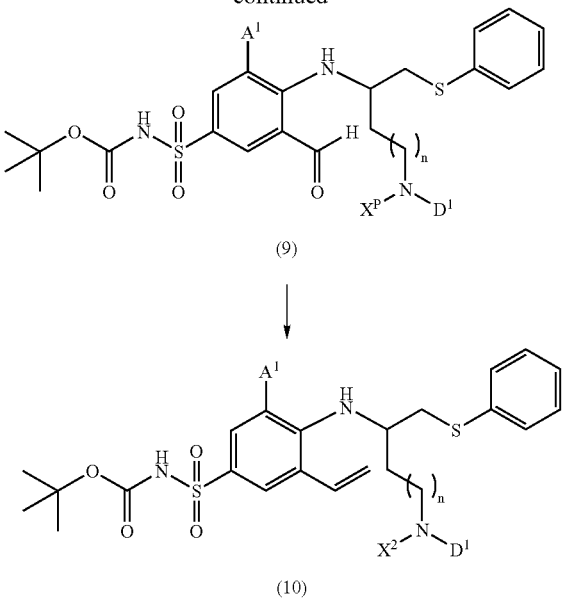

(9)

(10)

As shown in SCHEME 5, compounds having formula (9a) may be converted to compounds having formula (9) by reacting the former and DIBAL. Compounds having formula (9) may be converted to compounds having formula (10) by reacting the former and $Ph_3P=CH_2$ or $(CH_3CH_2O)_2P(O)CH_3$ and sodium hydride.

Compounds having formulas (4), (6), (7), (8) and (10) are examples of intermediates containing heterobifunctionality which may be used for intramolecular ring closures to prepare precursor compounds to compounds having formula (11),

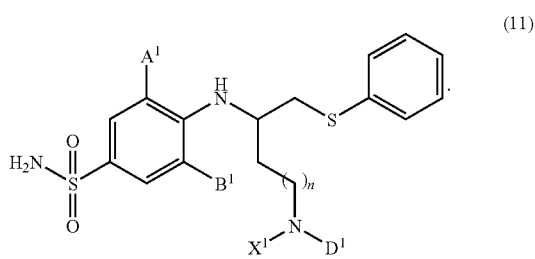

(11)

For example, when $X^2$ is $C_2$-$C_4$-alkyl substituted with Cl, Br or I, and an intramolecular OH is available, the compound may be treated with NaH to provide ethers; when $X^2$ is $C_2$-alkyl, $C_3$-alkyl or $C_4$-alkyl substituted with Cl, Br or I, and an intramolecular $NH_2$ or NH(alkyl) is available, the compound may be treated with potassium carbonate to provide amines; when $X^2$ is $C_2$-alkyl, $C_3$-alkyl or $C_4$-alkyl substituted with $NH_2$ or NH(alkyl), and an intramolecular $CO_2H$ is available, the compound may be treated with EDAC to provide amides; when $X^2$ is $C_2$-alkyl, $C_3$-alkyl or $C_4$-alkyl substituted with $CO_2H$, and an intramolecular $NH_2$ or NH(alkyl) is available, the compound may be treated with EDAC to provide amides; when $X^2$ is $C_2$-alkyl, $C_3$-alkyl or $C_4$-alkyl substituted with OH, and an intramolecular $CO_2H$ is available, the compound may be treated with EDAC to provide esters; when $X^2$ is $C_2$-alkyl, $C_3$-alkyl or $C_4$-alkyl substituted with $CO_2H$, and an intramolecular OH is available, the compound may be treated with EDAC to provide esters and when $X^2$ is $C_3$-alkenyl or $C_4$-alkenyl, and an intramolecular $C_2$-alkenyl or $C_3$-alkenyl is available, the compound may be treated with $MoCl_2(NO)(Ph_3P)_2 \cdot CH_3CH_2AlCl_2$ to provide alkenes which may be reduced with hydrogen and palladium to provide alkanes.

Compounds having formula (11) may be converted to compounds having formula (I) by reacting the former and compounds having formula $Z^1$—$CO_2H$ and a EDCI, with or without a DIEA.

Compounds having formula (11) may be converted to compounds having formula (I) by reacting the former and compounds having formula $Z^1$—COCl and the first base.

Reaction conditions (solvents, times, temperatures, concentrations) vary and are dependent on starting materials and products and whether the process is intermolecular or intramolecular.

The following examples are presented to provide what is believed to be the most useful and readily understood description of procedures and conceptual aspects of this invention.

Example 1A

2-Chloro-3-nitrobenzoic acid (5 g) and chlorosulfonic acid (30 mL) at 150° C. were stirred for 72 hours, cooled, added to ice and extracted ethyl acetate. The extract was washed with water and brine and dried ($Na_2SO_4$), filtered and concentrated. The concentrate in isopropyl alcohol (100 mL) and THF (100 mL) at −78° C. was treated with 38% ammonium hydroxide (30 mL), stirred for 2 hours, acidified with 12M hydrochloric acid and concentrated. The concentrate was partitioned between water and ethyl acetate. The extract was washed with water and brine and dried ($Na_2SO_4$), filtered and concentrated.

Example 1B

EXAMPLE 1A (4.5 g) and concentrated sulfuric acid (3 mL) in methanol (300 mL) at reflux was stirred overnight, cooled and concentrated. The concentrate was partitioned between water and ethyl acetate. The extract was washed with water and brine and dried ($Na_2SO_4$), filtered and concentrated. The concentrate was purified by chromatography on silica gel with 20% ethyl acetate/hexanes.

Example 1C 3-(R)-((Carbobenzyloxy)amino)-γ-butyrolactone, prepared as described in J. Am. Chem. Soc. 1986, 108, 4943-4952, (7.72 g) in THF (100 MnL) at ambient temperature was saturated with dimethylamine, stirred for 16 hours, and concentrated. The concentrate was filtered through silica gel with 50% acetone/hexanes.

Example 1D

EXAMPLE 1C (8.45 g), tributylphosphine (9.76 mL) and diphenyldisulfide (7.3 g) in toluene (15 mL) at 80° C. was stirred for 16 hours, cooled and concentrated. The concentrate was chromatographed on silica gel with 0-50% ethyl acetate/hexanes.

Example 1E

EXAMPLE 1D (7.5 g) and bis(cyclopentadienylzirconium (IV) chloride hydride (10.31 g) in THF (100 mL) under argon was stirred for 20 minutes at ambient temperature and concentrated. The concentrate was chromatographed on silica gel with 50% ethyl acetate/hexanes.

Example 1F

EXAMPLE 1E (4.5 g) in 1,2-dichloroethane (100 mL) was treated with 2-(methylamino)ethanol (1.5 g) and sodium triacetoxyborohydride (6.5 g), stirred at ambient temperature for 4 hours, diluted with dichloromethane, washed with 1M NaOH, water and brine and dried ($Na_2SO_4$), filtered and concentrated. The concentrate was chromatographed on silica gel with 6% ethyl acetate/ammonia-saturated dichloromethane and 5% methanol/ammonia-saturated dichloromethane.

Example 1G

EXAMPLE 1F ((6 g) was treated with 30% HBr in acetic acid (20 mL), stirred at ambient temperature overnight and partitioned between water and hexanes. The water layer was washed with hexane, made basic with solid $K_2HPO_4$ and NaOH (5 g), stirred for 4 hours at ambient temperature and concentrated. The concentrate was partitioned between ethyl acetate and water. The extract was washed with water and brine and dried ($NaSO_4$), filtered and concentrated.

Example 1H

EXAMPLE 1B (3.7 g), EXAMPLE 1G (3.2 g) and diisopropylethylamine (15 mL) in dimethylacetamide (50 mL) at 60° C. was stirred for 3 hours, cooled, diluted with ethyl acetate, washed with 20% $K_2HPO_4$, water and brine and dried ($Na_2SO_4$), filtered and concentrated. The concentrate was chromatographed on silica gel with 1, 2 and 3% methanol in ammonia-saturated dichloromethane.

Example 1I

EXAMPLE 1H (4.1 g) in dichloromethane (60 mL) at ambient temperature was treated with triethylamine (1.6 mL), di-tert-butyldicarbonate (1.93 g) and DMAP (97 mg), stirred overnight, diluted with ethyl acetate, washed with aqueous $NaHCO_3$, water and brine and dried ($Na_2SO_4$), filtered and concentrated. The concentrate was chromatographed on silica gel with 5 and 10% methanol in ammonia-saturated dichloromethane.

Example 1J

A solution of EXAMPLE 1I (1.2 g) in THF (10 mL), methanol (5 mL) and water (2.5 mL) at ambient temperature was treated with LiOH—$H_2O$ (364 mg), stirred overnight, neutralized with 2M HCl (4.5 mL) and concentrated with a toluene azeotrope.

Example 1K

EXAMPLE 1J (1.17 g), 2,2'-dipyridyl disulfide (518 mg) and triphenylphosphine (617 mg) in benzene (40 mL) at ambient temperature was stirred for 2 hours, treated with acetonitrile (100 mL) and added dropwise to a refluxing solution of silver perchlorate (1.24 g) in acetonitrile (150 mL). This mixture was refluxed for 1 hour and concentrated. The concentrate was partitioned between ethyl acetate and aqueous potassium cyanide. The extract was washed with water and brine and dried ($Na_2SO_4$), filtered and concentrated. The concentrate chromatographed on silica gel with 3-5% methanol/ammonia-saturated dichloromethane.

Example 1L

EXAMPLE 1K (30 mg), 4-(4,4-dimethylpiperidin-1-yl)benzoic acid, prepared as described in U.S. Pat. No. 6,720,338, (14.5 mg), DMAP (11.5 mg) and EDAC.HCl (18 mg) in dichloromethane (1 mL) at ambient temperature was stirred for 24 hours, concentrated, diluted with methanol (0.5 mL) and dimethylsulfoxide (0.5 mL) and purified by preparative HPLC on a 25 mm×100 mm Waters Symmetry $C_8$ column (7 μm particle size) with 10-100% acetonitrile/0.1% aqueous TFA over 8 minutes (run time: 10 minutes) at a flow rate of 40 mL/min. $^1$H NMR (300 MHz, DMSO-$d_6$) δ 12.14 (br, 1H), 10.10 (br), 9.74 (br, 1H), 8.49 (d, 1H), 8.17 (d, 1H), 8.05 (m, 1H), 7.77 (d, 2H), 7.58 (m, 1H), 7.03 (m, 3H), 6.93 (d, 2H), 6.83 (m, 2H), 5.16 (m, 1H), 3.77 (m, 12H), 2.93 (m, 3H), 2.27 (m, 1H), 2.09 (m, 1H), 1.37 (m, 4H), 0.94 (s, 6H).

Example 2

This example was prepared by substituting 4-(4-(2-(4-chlorophenyl)cyclohex-1-enylmethyl)piperazin-1-yl)benzoic acid, prepared as described in commonly-owned U.S. patent application Ser. No. 10/988,338, filed Nov. 12, 2004, for 4-(4,4-dimethylpiperidin-1-yl)benzoic acid in EXAMPLE 1L. $^1$H NMR (300 MHz, DMSO-$d_6$) δ 8.34 (s, 1H), 8.28 (d, 1H), 7.72 (d, 2H), 7.36 (d, 2H), 7.13 (m, 7H), 6.76 (d, 2), 3.80 (s, 3H), 3.10 (m, 4H), 2.75 (m, 2H), 2.27 (m, 4H), 2.18 (m, 6H), 1.99 (m, 2H), 1.88 (m, 2H), 1.65 (m, 4H).

Example 3

This example was prepared by substituting 4-(4-(4'-chloro-biphenyl-2-ylmethyl)piperazin-1-yl)benzoic acid, prepared as described in commonly-owned U.S. patent application Ser. No. 10/988,338, for 4-(4,4-dimethylpiperidin-1-yl)benzoic acid in EXAMPLE 1L. $^1$H NMR (300 MHz, DMSO-$d_6$) δ 10.19 (br, 1H), 9.82 (br, 2H), 8.48 (d, 1H), 8.15 (d, 1H), 8.04 (m, 1H), 7.80 (d, 2H), 7.73 (m, 1H), 7.58 (m, 5H), 7.36 (m, 3H), 7.00 (m, 5H), 6.81 (m, 2H), 5.14 (m, 1H), 3.19 (m, 23H).

Example 4

This example was prepared by substituting 4-(8-aza-spiro[4.5]dec-8-yl)-benzoic acid, prepared as described in U.S. Pat. No. 6,720,338, for 4-(4,4-dimethylpiperidin-1-yl)benzoic acid in EXAMPLE 1L. $^1$H NMR (300 MHz, DMSO-$d_6$) δ 12.15 (br, 1H), 10.08 (br, 1H), 9.72 (br, 1H), 8.49 (d, 1H), 8.17 (d, 1H), 8.05 (m, 1H), 7.75 (d, 2H), 7.04 (m, 3H), 6.93 (d, 2H), 6.83 (m, 2H), 5.16 (m, 1H), 3.76 (m, 12H), 2.92 (m, 3H), 2.27 (m, 1H), 2.09 (m, 1H), 1.59 (m, 4H), 1.43 (s, 8H).

Example 5

This example was prepared by substituting 4-(4-(2-trifluoromethylbenzylidene)piperidin-1-yl)benzoic acid, prepared as described in U.S. Pat. No. 6,720,338, for 4-(4,4-dimethylpiperidin-1-yl)benzoic acid in EXAMPLE 1L. $^1$H NMR (300 MHz, DMSO-$d_6$) δ 12.17 (br, 1H), 10.07 (br, 1H), 9.72 (br, 1H), 8.49 (d, 1H), 8.17 (d, 1H), 8.05 (m, 1H), 7.78 (d, 2H), 7.73 (d, 10H), 7.64 (t, 1H), 7.47 (t, 1H), 7.35 (d, 1H), 7.02 (m, 5H), 6.84 (m, 2H), 6.50 (s, 1H), 5.16 (m, 1H), 3.18 (m, 21H).

Example 6

This example was prepared by substituting 4'-fluoro-biphenyl-4-carboxylic acid, prepared as described in U.S. Pat. No. 6,720,338, for 4-(4,4-dimethylpiperidin-1-yl)benzoic acid in EXAMPLE 1L. $^1$H NMR (300 MHz, DMSO-$d_6$) δ 10.04 (br, 1H), 9.71 (br, 1H), 8.51 (d, 1H), 8.20 (d, 1H), 8.07 (m, 1H), 7.99 (d, 2H), 7.79 (m, 4H), 7.32 (t, 2H), 7.05 (m, 3H), 6.87 (m, 2H), 5.16 (m, 1H), 3.77 (m, 8H), 2.94 (m, 3H), 2.27 (m, 1H), 2.09 (m, 1H).

Example 7

This example was prepared by substituting 4-(4-methoxy-4-styryl-piperidin-1-yl)benzoic acid, prepared as described in commonly-owned U.S. patent application Ser. No. 10/988,338, for 4-(4,4-dimethylpiperidin-1-yl)benzoic acid in EXAMPLE 1L. $^1$H NMR (300 MHz, DMSO-$d_6$) δ 12.15 (br, 1H), 10.06 (br, 1H), 9.69 (br, 1H), 8.48 (d, 1H), 8.17 (d, 1H), 8.05 (m, 1H), 7.75 (d, 2H), 7.54 (d, 2H), 7.27 (m, 3H), 7.00 (m, 5H), 6.84 (m, 2H), 6.61 (d, 1H), 5.48 (d, 1H), 5.16 (m, 1H), 3.74 (m, 12H), 3.04 (s, 3H), 2.93 (m, 3H), 2.27 (m, 1H), 2.09 (m, 1H), 1.89 (m, 2H), 1.73 (m, 2H).

Example 8

This example was prepared by substituting 4-(4-(2-fluorobenzyl)-4-methoxypiperidin-1-yl)benzoic acid, prepared as described in commonly-owned U.S. patent application Ser. No. 10/988,338, for 4-(4,4-dimethylpiperidin-1-yl)benzoic acid in EXAMPLE 1L. $^1$H NMR (300 MHz, DMSO-$d_6$) δ 12.12 (br, 1H), 10.06 (br, 1H), 9.71 (br, 1H), 8.48 (d, 1H), 8.17 (m, 1H), 8.04 (m, 1H), 7.75 (d, 2H), 7.25 (m, 2H), 7.06 (m, 5H), 6.92 (d, 2H), 6.84 (m, 2H), 5.15 (m, 1H), 3.59 (m, 23H), 2.81 (s, 2H), 2.27 (m, 1H), 2.07 (m, 1H), 1.71 (m, 2H), 1.48 (m, 2H).

Example 9

This example was prepared by substituting 4-(4-biphenyl-2-ylmethyl-4-methoxypiperidin-1-yl)-benzoic acid, prepared as described in commonly-owned U.S. patent application Ser. No. 10/988,338, for 4-(4,4-dimethylpiperidin-1-yl)benzoic acid in EXAMPLE 1L. $^1$H NMR (300 MHz, DMSO-$d_6$) δ 12.11 (br, 1H), 10.06 (br, 1H), 9.71 (br, 1H), 8.48 (d, 1H), 8.17 (d, 1H), 8.04 (m, 1H), 7.71 (d, 2H), 7.33 (m, 9H), 7.15 (m, 1H), 7.02 (m, 3H), 6.82 (m, 4H), 5.16 (m, 1H), 3.74 (m, 11H), 3.02 (s, 3H), 2.88 (m, 6H), 2.27 (m, 1H), 2.07 (m, 1H), 1.46 (m, 2H), 1.17 (m, 2H).

Example 10

This example was prepared by substituting 4-(4-(2-(4-chlorophenyl)-4,4-dimethylcyclohex-1-enylmethyl)piperazin-1-yl)-benzoic acid, prepared as described in commonly-owned U.S. Provisional Application Ser. No. 60/233,866) for 4-(4,4-dimethylpiperidin-1-yl)benzoic acid in EXAMPLE 1L. $^1$H NMR (300 MHz, DMSO-$d_6$) δ 10.20 (br, 1H), 9.84 (br, 1H), 9.36 (br, 1H), 8.48 (d, 1H), 8.15 (m, 1H), 8.04 (m, 1H), 7.81 (d, 2H), 7.40 (d, 2H), 7.03 (m, 8H), 6.82 (m, 2H), 5.14 (m, 1H), 3.51 (m, 20H), 2.27 (m, 4H), 2.05 (m, 3H), 1.49 (m, 2H), 0.97 (s, 6H).

Example 11

This example was prepared by substituting 4-(4-(2-(4-chlorophenyl)cyclohept-1-enylmethyl)piperazin-1-yl)-benzoic acid, prepared as described in commonly-owned U.S. patent application Ser. No. 10/988,338, for 4-(4,4-dimethylpiperidin-1-yl)benzoic acid in EXAMPLE 1L. $^1$H NMR (300 MHz, DMSO-$d_6$) δ 10.21 (br, 1H), 9.85 (br, 1H), 9.30

(br, 1H), 8.48 (d, 1H), 8.15 (m, 1H), 8.04 (m, 1H), 7.81 (d, 2H), 7.41 (d, 2H), 7.11 (d, 2H), 7.01 (m, 6H), 6.82 (m, 2H), 5.14 (m, 1H), 3.20 (m, 27H), 1.82 (m, 2H), 1.57 (m, 4H).

Example 12

This example was prepared by substituting 4-(4-(3,3-diphenyl-allyl)-piperazin-1-yl)benzoic acid, prepared as described in commonly-owned U.S. patent application Ser. No. 10/988,338, for 4-(4,4-dimethylpiperidin-1-yl)benzoic acid in EXAMPLE 1L. $^1$H NMR (300 MHz, DMSO-$d_6$) δ 10.02 (br, 3H), 8.48 (d, 1H), 8.16 (m, 1H), 8.04 (m, 1H), 7.83 (d, 2H), 7.41 (m, 7H), 7.26 (m, 2H), 7.17 (m, 2H), 7.02 (m, 5H), 6.82 (m, 2H), 6.24 (t, 1H), 5.15 (m, 1H), 3.17 (m, 23H).

Example 13

This example was prepared by substituting 4-(4-(3,3-diphenylallyl)-piperazin-1-yl)benzoic acid, prepared as described in commonly-owned U.S. patent application Ser. No. 10/988,338, for 4-(4,4-dimethylpiperidin-1-yl)benzoic acid in EXAMPLE 1L. $^1$H NMR (300 MHz, DMSO-$d_6$) δ 12.23 (br, 1H), 10.17 (br, 1H), 9.80 (br, 1H), 8.48 (d, 1H), 8.16 (m, 1H), 8.03 (m, 1H), 7.79 (d, 2H), 7.70 (m, 1H), 7.43 (m, 7H), 6.99 (m, 5H), 6.82 (m, 2H), 5.14 (m, 1H), 3.18 (m, 25H).

Example 14

This example was prepared by substituting 4-(4-(2-trifluoromethyl-benzyl)-piperazin-1-yl)-benzoic acid, prepared as described in commonly-owned U.S. patent application Ser. No. 10/988,338, for 4-(4,4-dimethylpiperidin-1-yl)benzoic acid in EXAMPLE 1L. 11H N (300 MHz, DMSO-$d_6$) δ 12.20 (br, 1H), 10.16 (br, 1H), 9.79 (br, 1H), 8.48 (d, 1H), 8.16 (m, 1H), 8.05 (m, 1H), 7.81 (m, 5H), 7.60 (m, 1H), 7.04 (m 6H), 6.83 (m, 2H), 5.15 (m, 1H), 3.26 (m, 23H).

Example 15

This example was prepared by substituting 4-(4-(2-(4-chlorophenyl)-4,4-diethylcyclohexlmethyl)-piperazin-1-yl)-benzoic acid, prepared as described in commonly-owned U.S. Provisional Application Ser. No. 60/233,866, for 4-(4, 4-dimethylpiperidin-1-yl)benzoic acid in EXAMPLE 1L. $^1$H NMR (300 MHz, DMSO-$d_6$) δ 10.20 (br, 1H), 9.81 (br, 1H), 9.33 (br, 1H), 8.48 (d, 1H), 8.16 (d, 1H), 8.04 (m, 1H), 7.81 (d, 2H), 7.41 (d, 2H), 7.11 (d, 2), 7.01 (m, 6H), 6.82 (m, 2H), 5.15 (m, 1H), 3.51 (m, 22H), 2.23 (m, 3H), 2.02 (s, 2H), 1.51 (m, 2H), 1.30 (m, 4H), 0.79 (t, 6H).

Example 16

This example was prepared by substituting 4-(4-(4-(4-chlorophenyl)-tetrahydropyran-3-ylmethyl)-piperazin-1-yl)benzoic acid, prepared as described in commonly-owned U.S. patent application Ser. No. 10/988,338, for 4-(4,4-dimethylpiperidin-1-yl)benzoic acid in EXAMPLE 1L. $^1$H NMR (300 MHz, DMSO-$d_6$) δ 10.20 (br, 1H), 9.82 (br, 1H), 9.38 (br, 1H), 8.48 (d, 1H), 8.15 (m, 1H), 8.04 (m, 1H), 7.81 (d, 2H), 7.43 (d, 2H), 7.22 (d, 2H), 7.01 (m, 6H), 6.82 (m, 2H), 5.14 (m, 1H), 3.16 (m, 29H).

Example 17

This example was prepared by substituting 3-phenoxybenzoic acid for 4-(4,4-dimethylpiperidin-1-yl)benzoic acid in EXAMPLE 1L. $^1$H NMR (300 MHz, DMSO-$d_6$) δ 10.01 (br, 1H), 9.68 (br, 1H), 8.47 (d, 1H), 8.14 (m, 1H), 7.97 (m, 1H), 7.70 (m, 1H), 7.46 (m, 2H), 7.36 (m, 2H), 7.23 (m, 1H), 7.15 (m, 1H), 7.03 (m, 5H), 6.85 (m, 2H), 5.14 (m, 1H), 3.75 (m, 8H), 2.93 (m, 3H), 2.27 (m, 1H), 2.07 (m, 1H).

Example 18A

EXAMPLE 1E (3 g) in 1,2-dichloroethane (50 mL) at ambient temperature was treated with 3-amino-1-propanol (3.75 g) and sodium triacetoxyborohydride (2.9 g), stirred for 2 hours, treated with methanol (50 mL) and sodium triacetoxyborohydride (3 g) were added, stirred overnight and concentrated. The concentrate was partitioned between ethyl acetate and 1M NaOH. The extract was washed with water and brine and dried ($Na_2SO_4$), filtered and concentrated.

Example 18B

EXAMPLE 18A (1.5 g) in dichloromethane (5 mL) at ambient temperature was treated with 37% aqueous formaldehyde (5 mL) and acetic acid (5 mL), stirred for 15 minutes, treated with sodium cyanoborohydride (5 g) in methanol (15 mL), stirred for 2 hours and concentrated. The concentrate was partitioned between ethyl acetate and 1M NaOH. The extract was washed with water and brine and dried ($Na_2SO_4$), filtered and concentrated.

Example 18C

This example was prepared by substituting EXAMPLE 18B for EXAMPLE 1F in EXAMPLE 1G.

Example 18D

This example was prepared by substituting EXAMPLE 18C for EXAMPLE 1G in EXAMPLE 1H.

Example 18E

This example was prepared by substituting EXAMPLE 18D for EXAMPLE 1I in EXAMPLE 1J.

Example 18F

EXAMPLE 18E (120 mg), bis(2-oxo-3-oxazolidinyl) phosphonic chloride (100 mg), TEA (3 mL) and DMAP (20 mg) in dichloromethane (5 mL) at ambient temperature was stirred overnight, concentrated and reconcentrated twice from methanol/dichloromethane.

Example 18G

This example was prepared by substituting EXAMPLE 18F and 4-(4-(2-(4-chlorophenyl)cyclohex-1-enylmethyl) piperazin-1-yl)benzoic acid, prepared as described in commonly-owned U.S. patent application Ser. No. 10/988,338, for EXAMPLE 1K and 4-(4,4-dimethylpiperidin-1-yl)benzoic acid, respectively, in EXAMPLE 1L. $^1$H NMR (500 MHz, DMSO-$d_6$) δ 8.45 (s, 1H), 8.06 (m, 1H), 7.73 (d, 2H), 7.37 (d, 2H), 7.11 (m, 7H), 6.85 (d, 2H), 4.55 (s, 3H), 4.10 (m, 4H), 3.18 (m, 6H), 2.75 (m, 2H), 2.27 (m, 4H), 2.18 (m, 6H), 1.88 (m, 2H), 1.88 (m, 2H), 1.67 (m, 4H).

We claim:
1. A compound having formula (I),

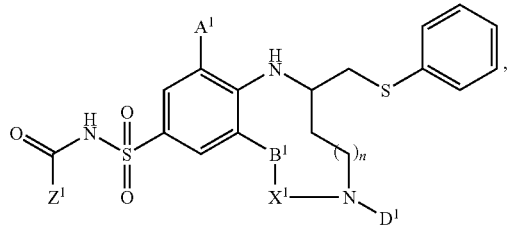

or a therapeutically acceptable salt thereof, wherein
$A^1$ is CN, $NO_2$, C(O)OH, F, Cl, Br, $CF_3$, $OCF_3$, $CF_2CF_3$, $OCF_2CF_3$, $C(O)R^1$, $C(O)OR^1$, $SR^1$, $C(O)NH_2$, $C(O)NHR^1$, $C(O)N(R^1)_2$, $NHS(O)R^1$, $SO_2NHR^1$, $S(O)R^1$, or $SO_2R^1$;

n is 1, 2 or 3;

$R^1$ is $R^2$, $R^3$, $R^4$ or $R^5$;

$R^2$ is alkyl, alkenyl or alkynyl;

$R^3$ is perhaloalkyl or perhaloalkenyl;

$R^4$ is $C_1$-alkyl or $C_2$-alkenyl, each of which is unsubstituted or substituted with one or two of independently selected F, Cl or Br;

$R^5$ is $C_2$-$C_6$-alkyl or $C_3$-$C_6$-alkenyl, each of which is unsubstituted or substituted with one or two or three or four of independently selected F, Cl or Br;

$B^1$ and $X^1$ taken together are alkylene, unsubstituted or substituted with =O and having one $CH_2$ moiety unreplaced or replaced with CHCH, O, NH or N(alkyl);

$D^1$ is H, alkyl or phenyl;

$Z^1$ is $Z^2$, $Z^3$ or $Z^4$;

$Z^2$ is phenyl or heteroaryl, each of which is substituted with $R^6$, $OR^6$, $SR^6$, $S(O)R^6$ or $SO_2R^6$;

$R^6$ is phenyl, heteroaryl, cycloalkyl, cycloalkenyl, heterocycloalkyl or heterocycloalkenyl, each of which is unsubstituted or substituted with one or two of independently selected alkyl, spiroalkyl, F, Cl, Br, I, $R^7$, $OR^7$, $SR^7$, $S(O)R^7$, or $SO_2R^7$;

$R^7$ is alkyl, alkenyl or alkynyl;

$Z^3$ is phenyl or heteroaryl, each of which is substituted with cycloalkyl, cycloalkenyl, heterocycloalkyl or heterocycloalkenyl, each of which is substituted with $CHR^8$;

$R^8$ is phenyl, heteroaryl, cycloalkyl, cycloalkenyl, heterocycloalkyl or heterocycloalkenyl, each of which is unsubstituted or substituted with one or two or three of independently selected F, Cl, Br, I, OH, C(O)OH, C(O)OCH_3, CN, $NH_2$, $NH(CH_3)$, $N(CH_3)_2$, $CF_3$, $OCF_3$, $CF_2CF_3$ or $OCF_2CF_3$;

$Z^4$ is phenyl or heteroaryl, each of which is substituted with phenyl, heteroaryl, cycloalkyl, cycloalkenyl, heterocycloalkyl or heterocycloalkenyl, each of which is substituted with one or two of $R^9$ or $OR^9$;

$R^9$ is alkyl, alkenyl or alkynyl, each of which is substituted with one or two of independently selected phenyl, heteroaryl cycloalkyl, cycloalkenyl, heterocycloalkyl or heterocycloalkenyl, each of which is unsubstituted or substituted with one or two or three of independently selected alkyl, alkenyl, alkynyl, F, Cl, Br, I, OH, C(O)OH, C(O)OCH_3, CN, $NH_2$, $NH(CH_3)$, $N(CH_3)_2$, $CF_3$, $OCF_3$, $CF_2CF_3$, $OCF_2CF_3$ or $R^{11}$; and $R^{11}$ is phenyl or heteroaryl, each of which is unsubstituted or substituted with one or two or three of F, Cl, Br, I, OH, C(O)OH, C(O)OCH_3, CN, $NH_2$, $NH(CH_3)$, $N(CH_3)_2$, $CF_3$, $OCF_3$, $CF_2CF_3$, $OCF_2CF_3$.

2. The compound of claim 1 wherein $A^1$ is $NO_2$; n is 1, 2 or 3;

$B^1$ and $X^1$ together are alkylene, which is unsubstituted or substituted with =O and having one $CH_2$ moiety unreplaced or replaced with CHCH, O, NH or N(alkyl);

$D^1$ is H, alkyl or phenyl;

$Z^1$ is $Z^2$, $Z^3$ or $Z^4$;

$Z^2$ is phenyl substituted with $R^6$, $OR^6$, $SR^6$, $S(O)R^6$ or $SO_2R^6$;

$R^6$ is phenyl or heterocycloalkyl, each of which is unsubstituted or substituted with one or two of independently selected alkyl, spiroalkyl, F, Cl, Br or I;

$Z^3$ is phenyl substituted with heterocycloalkyl which is substituted with $CHR^8$;

$R^8$ is phenyl substituted with one or two or three of independently selected F, Cl, Br, I, OH, C(O)OH, C(O)OCH_3, CN, $NH_2$, $NH(CH_3)$, $N(CH_3)_2$, $CF_3$, $OCF_3$, $CF_2CF_3$ or $OCF_2CF_3$;

$Z^4$ is phenyl substituted with heterocycloalkyl which is substituted with one or two of $R^9$ or $OR^9$;

$R^9$ is alkyl or alkenyl, each of which is substituted with one or two of independently selected phenyl, cycloalkenyl or heterocycloalkenyl, each of which is unsubstituted or substituted with one or two or three of independently selected alkyl, alkenyl, alkynyl, F, Cl, Br, I, OH, C(O)OH, C(O)OCH_3, CN, $NH_2$, $NH(CH_3)$, $N(CH_3)_2$, $CF_3$, $OCF_3$, $CF_2CF_3$ or $R^{11}$; and $R^{11}$ is phenyl which is unsubstituted or substituted with one or two or three of F, Cl, Br, I, OH, C(O)OH, C(O)OCH_3, CN, $NH_2$, $NH(CH_3)$, $N(CH_3)_2$, $CF_3$, $OCF_3$, $CF_2CF_3$, $OCF_2CF_3$.

3. The compound of claim 2, wherein $A^1$ is $NO_2$; n is 1; $B^1$ and $X^1$ taken together are alkylene substituted with =O and having one $CH_2$ moiety replaced with O;

$D^1$ is alkyl;

$Z^1$ is $Z^2$, $Z^3$ or $Z^4$;

$Z^2$ is phenyl substituted with $R^6$ or $OR^6$;

$R^6$ is phenyl, piperidinyl or piperazinyl, each of which is unsubstituted or substituted with one or two of independently selected alkyl, spiroalkyl, F, Cl, Br or I;

$Z^3$ is phenyl substituted with heterocycloalkyl which is substituted with $CHR^8$;

$R^8$ is phenyl substituted with one or two or three of independently selected F, Cl, Br, I, $CF_3$ or $OCF_3$;

$Z^4$ is phenyl substituted with piperidinyl or piperazinyl, each of which is substituted with one or two of $R^9$ or $OR^9$;

$R^9$ is alkyl or alkenyl, each of which is substituted with one or two of independently selected phenyl, cycloalkenyl or heterocycloalkenyl, each of which is unsubstituted or substituted with one or two or three of independently selected alkyl, alkenyl, alkynyl, F, Cl, Br, I, OH, C(O)OH, C(O)OCH_3, CN, $NH_2$, $NH(CH_3)$, $N(CH_3)_2$, $CF_3$, $OCF_3$ or $R^{11}$; and $R^{11}$ is phenyl which is unsubstituted or substituted with one or two or three of F, Cl, Br, I, OH, $CF_3$ or $OCF_3$.

4. The compound according to claim 1 or a pharmaceutically acceptable salt thereof, selected from the group consisting of:
(2R)-N-(4-(4,4-dimethylpiperidin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide;
(2R)-N-(4-(4-((2-(4-chlorophenyl)-1-cyclohexen-1-yl)methyl)piperazin-1-yl)benzoyl)-5-methyl-13-nitro-9- oxo-2-((phenylsulfanyl)methyl)-1,2,3,4,5,6,7,9-octahydro-8,1,5-benzoxadiazacycloundecine-11-sulfonamide;

(2R)-N-(4-(4-((4'-chloro(1,1'-biphenyl)-2-yl)methyl)piperazin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide;

(2R)-N-(4-(8-azaspiro[4.5]dec-8-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide;

(2R)-5-methyl-13-nitro-9-oxo-2-((phenylsulfanyl)methyl)-N-(4-(4-(2-(trifluoromethyl)benzylidene)piperidin-1-yl)benzoyl)-1,2,3,4,5,6,7,9-octahydro-8,1,5-benzoxadiazacycloundecine-11-sulfonamide;

(2R)-N-((4'-fluoro(1,1'-biphenyl)-4-yl)carbonyl)-5-methyl-13-nitro-9-oxo-2-((phenylsulfanyl)methyl)-1,2,3,4,5,6,7,9-octahydro-8,1,5-benzoxadiazacycloundecine-11-sulfonamide;

(2R)-N-(4-(4-methoxy-4-((Z)-2-phenylethenyl)piperidin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide;

(2R)-N-(4-(4-(2-fluorobenzyl)-4-methoxypiperidin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide;

(2R)-N-(4-(4-((1,1'-biphenyl)-2-ylmethyl)-4-methoxypiperidin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide;

(2R)-N-(4-(4-((2-(4-chlorophenyl)-4,4-dimethylcyclohex-1-en-1-yl)methyl)piperazin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide;

(2R)-N-(4-(4-((2-(4-chlorophenyl)cyclohept-1-en-1-yl)methyl)piperazin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide;

(2R)-N-(4-(4-(3,3-diphenyl-2-propenyl)piperazin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide;

(2R)-N-(4-(4-((1,1'-biphenyl)-2-ylmethyl)piperazin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide;

(2R)-5-methyl-13-nitro-9-oxo-2-((phenylsulfanyl)methyl)-N-(4-(4-(2-(trifluoromethyl)benzyl)piperazin-1-yl)benzoyl)-1,2,3,4,5,6,7,9-octahydro-8,1,5-benzoxadiazacycloundecine-11-sulfonamide;

(2R)-N-(4-(4-((2-(4-chlorophenyl)-4,4-diethylcyclohex-1-en-1-yl)methyl)piperazin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide;

(2R)-N-(4-(4-((4-(4-chlorophenyl)-5,6-dihydro-2H-pyran-3-yl)methyl)piperazin-1-yl)benzoyl)-5-methyl-13-nitro-9-oxo-2-((phenylsulfanyl)methyl)-1,2,3,4,5,6,7,9-octahydro-8,1,5-benzoxadiazacycloundecine-11-sulfonamide;

(2R)-5-methyl-13-nitro-9-oxo-N-(3-phenoxybenzoyl)-2-((phenylsulfanyl)methyl)-1,2,3,4,5,6,7,9-octahydro-8,1,5-benzoxadiazacycloundecine-11-sulfonamide; and (2R)-N-(4-(4-((2-(4-chlorophenyl)-1-cyclohexen-1-yl)methyl)piperazin-1-yl)benzoyl)-5-methyl-14-nitro-10-oxo-2-((phenylsulfanyl)methyl)-1,3,4,5,6,7,8,10-octahydro-2H-9,1,5-benzoxadiazacyclododecine-12-sulfonamide.

* * * * *